United States Patent
Ogawa

(10) Patent No.: US 8,192,770 B2
(45) Date of Patent: Jun. 5, 2012

(54) ENZYME PREPARATION FOR ADHESION-MOLDED FOODS AND METHOD FOR PRODUCING ADHESION-MOLDED FOOD

(75) Inventor: Teppei Ogawa, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 13/029,595

(22) Filed: Feb. 17, 2011

(65) Prior Publication Data

US 2011/0206803 A1    Aug. 25, 2011

Related U.S. Application Data

(63) Continuation of application No. PCT/JP2009/066873, filed on Sep. 18, 2009.

(30) Foreign Application Priority Data

Sep. 25, 2008    (JP) .................. 2008-246480

(51) Int. Cl.
A23L 1/314    (2006.01)

(52) U.S. Cl. ................. 426/7; 426/63; 426/641

(58) Field of Classification Search ............ 426/7, 63, 426/641
See application file for complete search history.

(56) References Cited

U.S. PATENT DOCUMENTS

| 4,917,904 A | 4/1990 | Wakameda et al. |
|---|---|---|
| 5,518,742 A | 5/1996 | Soeda et al. |
| 5,658,605 A | 8/1997 | Soeda et al. |
| 5,968,568 A | 10/1999 | Kuraishi et al. |
| 2004/0131728 A1 | 7/2004 | Ootsuka et al. |
| 2005/0249839 A1 | 11/2005 | Ishida et al. |
| 2007/0054346 A1 | 3/2007 | Nakagoshi et al. |
| 2010/0086641 A1 | 4/2010 | Ishida et al. |
| 2010/0136167 A1 | 6/2010 | Yamada et al. |

FOREIGN PATENT DOCUMENTS

| JP | 64-10949 | 1/1989 |
|---|---|---|
| JP | 4-207194 | 7/1992 |
| JP | 6-284867 | 10/1994 |
| JP | 1927253 B | 4/1995 |
| JP | 8-298962 | 11/1996 |
| JP | 3353383 B2 | 12/2002 |
| JP | 3353503 62 | 12/2002 |
| JP | 2003-47441 | 2/2003 |
| JP | 3407599 B2 | 5/2003 |
| JP | 2006-246716 | 9/2006 |
| WO | WO 02/080700 A1 | 10/2002 |
| WO | WO 2004/028274 A1 | 4/2004 |
| WO | WO 2007/026921 A1 | 3/2007 |
| WO | WO 2008/120798 A1 | 10/2008 |

OTHER PUBLICATIONS

U.S. Appl. No. 08/563,587, filed Nov. 28, 1995, Sakai, et al.
Notification of Transmittal of Translation of the International Preliminary Report, International Preliminary Report on Patentability and Written Opinion issued May 19, 2011 in PCT/JP2009/066873.
International Search Report issued Dec. 8, 2009 in Application No. PCT/JP2009/066873.

*Primary Examiner* — D. Lawrence Tarazano
*Assistant Examiner* — Hamid R Badr
(74) *Attorney, Agent, or Firm* — Oblon, Spivak, McClelland, Maier & Neustadt, L.L.P.

(57) ABSTRACT

By using transglutaminase with calcium chloride or magnesium chloride as active ingredients, food raw materials such as meat pieces can be sufficiently adhesion-molded without using a protein material.

21 Claims, 1 Drawing Sheet

ENZYME PREPARATION FOR ADHESION-MOLDED FOODS AND METHOD FOR PRODUCING ADHESION-MOLDED FOOD

CROSS REFERENCES TO RELATED APPLICATIONS

This application is a continuation of International Patent Application No. PCT/JP2009/066873, filed on Sep. 18, 2009, and claims priority to Japanese Patent Application No. 246480/2008, filed on Sep. 25, 2008, both of which are incorporated herein by reference in their entireties.

BACKGROUND OF THE INVENTION

1. Field of the Invention

The present invention relates to enzyme preparations for bound and formed foods, and methods for producing a bound and formed food. The present invention also relates to bound and formed foods produced by such a method.

2. Discussion of the Background

There are many reports concerning techniques on binding food raw materials using transglutaminase. Japanese Patent No. 1927253 discloses a technique to produce a bound and formed food with the use of only transglutaminase. The technique described in this patent is groundbreaking in the sense that it developed a novel use of transglutaminase. However, because of insufficient binding strength, techniques using a variety of other components with transglutaminase have been studied, and put into practical application.

Japanese Patent Nos. 3353383 and 3353503 disclose bound and formed foods, in which transglutaminase and its substrate caseins are used in combination. The methods described in these patents are applicable to a wide range of food raw materials, including not only livestock meat, but fishery products such as fish meat, squid, and crab, and fish roe such as salmon roe, herring roe, salted salmon roe, and salted cod roe. The methods described in these patents are inventions concerning highly versatile binding and forming methods that enable a food to be bound in the raw state without influencing taste and flavor.

Because of recent problems of food allergies, the use of milk-derived proteins for processed foods is not always possible. In this connection, binding methods that use transglutaminase and non-casein proteins have been studied. Japanese Patent No. 3407599 discloses a binding and forming method that uses collagen and transglutaminase as the active ingredients without using casein. However, because collagen has the property to develop a high viscosity when dissolved in water, the method requires the collagen to be dissolved in cold water of 10° C. or less, and the bonding procedure must immediately follow the dissolving of the collagen. The method is therefore problematic in terms of handling. It should also be noted that the binding strength is weak in the absence of a salt, and practical effects cannot be expected in this case.

In this connection, International Publication WO 02/080700 discloses an enzyme preparation for binding food raw materials, and a method of production of bound and formed food using the enzyme preparation. The invention described in this publication uses a specific collagen in which the total number of hydroxyproline and proline residues (hereinafter, also referred to as "imino acids") is less than 20% of the total amino acid residues in the collagen, and the specific collagen and transglutaminase are contained as the active ingredients. JP-A-2006-246716 describes suppressing the gelling of collagen at low temperatures by preferably blending salts, for example, potassium chloride, and calcium chloride, to form an adhesive containing transglutaminase, collagen, and salts for a bound and formed food. However, because the invention described in JP-A-2006-246716 uses calcium chloride to suppress the gelling of collagen at low temperatures, the invention of this publication is completely different in the way calcium chloride is used in the present invention, as will be described later. Accordingly, the invention described in JP-A-2006-246716 does not suggest the present invention.

Further, the type of collagen that can be used as the specific collagen is essentially fish skin-derived collagen. As such, there are cases where preparations that contain fish collagen are not usable for livestock meat processed products that use pork, beef, and chicken, because fish collagen has a different protein origin from these products. Particularly in the European market where processed foods that use raw materials originating in fish must be labeled with a listing of allergenic ingredients, the use of fish collagen for livestock meat processed products is often more restricted than in other regions.

The binding techniques currently available all use specific protein materials in a blend, and no technique is available that can satisfy the need to be free of different proteins. Despite the need for a binding technique that does not use protein materials, no technique has been developed that can provide practical levels of binding strength without using protein materials.

SUMMARY OF THE INVENTION

Accordingly, it is one object of the present invention to provide novel enzyme preparations for binding and forming a bound and formed food.

It is another object of the present invention to provide novel enzyme preparations for binding and forming a bound and formed food, with which food raw materials such as meat pieces can be sufficiently bound and formed without using protein materials.

It is another object of the present invention to provide novel methods for preparing a bound and formed food by using such an enzyme preparation.

It is another object of the present invention to provide novel bound and formed foods which are prepared by such a method.

These and other objects, which will become apparent during the following detailed description, have been achieved by the inventor's discovery that food raw materials such as livestock meat can be bound with the use of transglutaminase and calcium chloride or magnesium chloride.

Thus, the present invention provides:

(1) An enzyme preparation for preparing a bound and formed food, comprising transglutaminase, and calcium chloride or magnesium chloride as active ingredients, wherein the amount of calcium chloride is 0.007 to 0.03 g per 1 U of the transglutaminase in said enzyme preparation, or wherein the amount of magnesium chloride is 0.022 to 0.025 g per 1 U of the transglutaminase in said enzyme preparation.

(2) A method for producing a bound and formed food, comprising adding 0.6 g of calcium chloride and 75 to 100 units of transglutaminase per 100 g of a food raw material.

(3) A method for producing a bound and formed food, comprising adding 0.7 to 0.9 g of calcium chloride and 25 to 100 units of transglutaminase per 100 g of a food raw material.

(4) A method for producing a bound and formed food, comprising adding 1.4 to 1.6 g of magnesium chloride and 60 to 100 units of transglutaminase per 100 g of a food raw material.

(5) A method according to any of (2) to (4), wherein the food raw material is meat, and wherein the bound and formed food is bound and formed meat.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
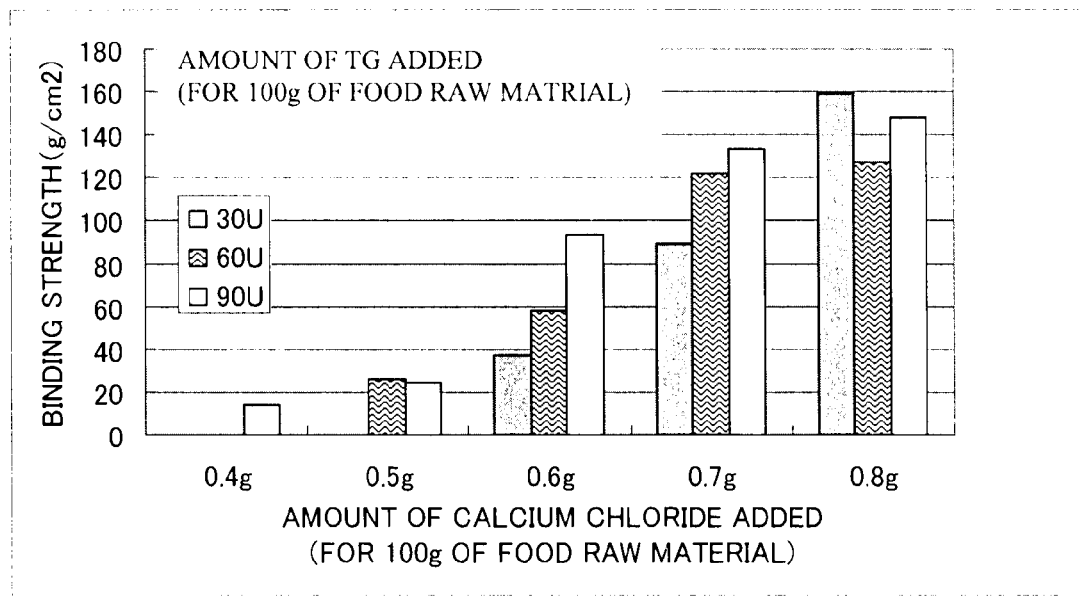
FIG. 1 is a diagram representing the relationship between the binding strength and the amounts of calcium chloride and transglutaminase added (Example 1)

The transglutaminase to be used in the present invention is an enzyme used for catalyzing an acyl-transfer reaction in a γ-carboxyamide group in a glutamine residue in a protein or peptide chain. An ε-(γ-Glu)-Lys bond is formed in and between protein molecules by the action of the transglutaminase as an acyl receptor exerted on an ε-amino group of a lysine residue in the protein. An enzyme of any origin can be used as the transglutaminase to be used in the present invention, as long as it has transglutaminase activity. For example, enzymes that originate in microorganisms, such as those from actinomycetes (see, Japanese Patent No. 2572716, which is incorporated herein by reference), and from *Bacillus subtilis* (see, Japanese Patent No. 3873408, which is incorporated herein by reference) can be used. Further, the enzyme may be of guinea pig liver origin (see, Japanese Patent No. 1689614, which is incorporated herein by reference), microorganism origin (see, WO96/06931, which is incorporated herein by reference), animal origin including cow blood and pig blood, fish origin including salmon and red sea bream (see, Seki et al., *Nippon Suisan Gakkaishi*, 1990, 56, 125-132, which is incorporated herein by reference), or oyster origin (see, U.S. Pat. No. 5,736,356, which is incorporated herein by reference). Further, for example, the enzyme may be those produced by genetic recombination (see, for example, Japanese Patent No. 3010589, JP-A-11-75876, WO01/23591, WO02/081694, and WO2004/078973, all of which are incorporated herein by reference). That is, any transglutaminase can be used in the present invention, and the origin and method of production are not limited. However, considering functionality for food applications and ease of handling, it is preferable to use transglutaminases of microorganism origin (Japanese Patent No. 2572716), which can be commercially mass-produced, and are available at low cost.

The activity unit of the transglutaminase used in the present invention is measured and defined as follows. Specifically, a reaction is performed by using benzyloxycarbonyl-L-glutaminylglycine and hydroxylamine as a substrate, and, after converting the thus-generated hydroxamic acid into an iron complex in the presence of trichloroacetic acid, the amount of the iron complex is measured at an absorbance of 525 nm. An enzyme amount that enables generation of 1 micromole of hydroxamic acid in one minute is defined as 1 unit which is an activity unit of transglutaminase. Details of this measurement method which is called hydroxamate method have already been reported (see, for example, Japanese Patent No. 2572716).

The essential components calcium chloride and magnesium chloride in the present invention may be of any grade, provided that they are usable for food. Calcium chloride or magnesium chloride may be used alone, or calcium chloride and magnesium chloride may be used in combination. The use of calcium chloride and/or magnesium chloride considerably increases the binding effect.

In the enzyme preparation of the present invention, the mixture ratio of the constituent components transglutaminase and calcium chloride or magnesium chloride is such that the calcium chloride content is preferably 0.007 to 0.03 g per 1 U of transglutaminase in the preparation, or the magnesium chloride content is preferably 0.022 to 0.025 g per 1 U of transglutaminase in the enzyme preparation. The transglutaminase is mixed in 1 to 200 units per gram of the enzyme preparation.

The enzyme preparation for binding of the present invention comprises transglutaminase and calcium chloride and/or magnesium chloride as the active ingredients, and may additionally comprise other components, including, for example, known food excipients such as lactose, sucrose, maltitol, sorbitol, dextrin, branched dextrin, cyclodextrin, silicon dioxide, cellulose, starches, polysaccharides, gums, and pectin. The enzyme preparation may also comprise sodium bicarbonate, sodium citrate, sodium phosphate, calcined calcium, calcium phosphate, calcium carbonate, magnesium carbonate, sodium chloride, potassium chloride or various polyphosphates such as sodium pyrophosphate, sodium tripolyphosphate, or sodium metaphosphate. It is also possible to appropriately mix components such as flavor enhancers, sugars, spices, artificial colors, coloring agents, ascorbic acids and salts thereof, emulsifiers, or fats and oils.

The enzyme preparation for binding and forming of the present invention is not necessarily required to be provided as a mixture of transglutaminase and calcium chloride or magnesium chloride contained in the same container, and may be provided in the form of a kit that contains these components in separate containers. The enzyme preparation may be a powder or a liquid.

In the present invention, the bound and formed food refers to food products obtained by binding and forming food raw material pieces measuring 3 mm or more, preferably 1 cm or more in the smallest side, and excludes paste products, such as sausage and kamaboko, produced from minced or paste raw materials. Any food raw material may be used as long as the material is a protein-based food. Examples of food raw material include meat such as beef, pork, horse, mutton, goat, rabbit, chicken, duck, and domestic duck; various types of fish meat; shellfish; crustaceans such as shrimp and crab; mollusks such as squid and octopus; and fish roe such as salmon roe, and salted salmon roe. These are merely examples, and the food raw material is not limited to these.

Binding of food pieces or small food materials requires a tensile strength of 80 g/cm$^2$ or more as measured with a rheometer (Fudo Kougyou). A tensile strength less than 80 g/cm$^2$ is not suited for practical use, because it causes the materials to detach during the production or preparation of a bound and formed food. Thus, the binding strength of the bound and formed food prepared by the present method is at least 80 g/cm$^2$, preferably at least 85 g/cm$^2$, more preferably at least 90 g/cm$^2$, even more preferably at least 95 g/cm$^2$, still more preferably at least 100 g/cm$^2$.

As described above, the present invention is applicable to all kinds of protein-based food raw materials, enabling the production of bound and formed products without addition of protein materials (purified protein or extracted protein) such as casein and collagen. The present invention can therefore solve the problem of the meat processing industry looking for ways to be free of different proteins, and to be free of the need to put a labeling of allergic ingredients.

The following methods can be used to produce a bound and formed food by binding food raw materials.

A method using an enzyme preparation that comprises transglutaminase and calcium chloride or magnesium chloride as the active ingredients; or A method using transglutaminase and calcium chloride or magnesium chloride that are separately purchased.

Either method is usable.

In either case, the calcium chloride is used in an amount of preferably from 0.6 to 0.9 g (inclusive), more preferably from 0.6 to 0.8 g, in terms of a weight of dihydrate crystals, per 100 g of the food raw material. Above 0.9 g, the taste of calcium chloride becomes strong, and the bound and formed food cannot have good taste. Below 0.6 g, sufficient binding cannot be obtained even with the use of transglutaminase, and binding becomes insufficient in the bound and formed food.

The transglutaminase is used in an amount of preferably 75 to 100 units, more preferably 90 to 100 units per 100 g of the food raw material when the calcium chloride content is 0.6 g per 100 g of the food raw material. When the calcium chloride content is 0.7 to 0.9 g per 100 g of the food raw material, the transglutaminase is used in an amount of preferably 20 to 100 units, more preferably 30 to 90 units per 100 g of the food raw material. When the transglutaminase is used in amounts below these ranges, binding does not develop sufficiently. Above these ranges, the cost of the transglutaminase becomes too much of a factor.

The magnesium chloride is used in an amount of preferably 1.4 to 1.6 g, in terms of a weight of hexahydrate crystals, per 100 g of the food raw material. Above 1.6 g, the taste of the magnesium chloride becomes strong, and the bound and formed food cannot have good taste. Below 1.4 g, sufficient binding cannot be obtained even with the use of the transglutaminase, and binding becomes insufficient in the bound and formed food. The transglutaminase is used in an amount of preferably 60 to 100 units per 100 g of the food raw material when the magnesium chloride content is 1.4 to 1.6 g per 100 g of the food raw material. When the transglutaminase is used in amounts below this range, binding does not develop sufficiently. Above this range, the cost of the transglutaminase becomes too much of a factor.

Note that sufficient binding is the state in which the tensile strength as measured with a rheometer is 80 g/cm$^2$ or more.

Production of a bound and formed food by the binding of food raw materials can use either a method in which the enzyme preparation for binding of the present invention is used by being dissolved in a solvent, or a method in which the enzyme preparation is mixed with food raw materials in powdery form. Specifically, the essential components transglutaminase, calcium chloride, and magnesium chloride are mixed with the food raw materials either separately or at the same time in the form of a solution or a powder. Both of these methods are contained within the method for producing bound and formed foods of the present invention.

The bound food may be prepared by contacting the food raw material with the enzyme preparation at any suitable temperature for any suitable time sufficient to produce a bound food having the desired binding strength. Selection of the appropriate time and temperature for a particular food raw material(s) is within the abilities of one skilled in the art. However, good results have been achieved by using a time of 10 seconds to 48 hours, preferably 5 minutes to 48 hours, more preferably 10 minutes to 24 hours, and a temperature of 0 to 60° C., preferably 0 to 40° C., more preferably 0 to 20° C.

Other features of the invention will become apparent in the course of the following descriptions of exemplary embodiments which are given for illustration of the invention and are not intended to be limiting thereof.

EXAMPLES

Example 1

A commercially available transglutaminase (Activa TG; Ajinomoto Co., Inc.; specific activity, 1,000 units/g) of *Streptomyces mobaraensis* origin was used as the transglutaminase. Note that *Streptomyces mobaraensis* had been called *Streptoverticillium mobaraense* before 1990. Magnesium chloride hexahydrate (from Tomita Pharmaceutical Co., Ltd.) and calcium chloride dehydrate (from Tomita Pharmaceutical Co., Ltd.) were used. Transglutaminase and either calcium chloride or magnesium chloride, in the amounts shown in Tables 1 and 2, were weighed and dissolved in 12 ml of water. The resulting mixed solutions were then used as enzyme preparations of the present invention.

TABLE 1

Formulations of Enzyme Preparations.

| | Component | |
|---|---|---|
| Test Group | Transglutaminase (U) | Calcium chloride (g) |
| 1 | 90 | 1.2 |
| 2 | 90 | 1.5 |
| 3 | 90 | 1.8 |
| 4 | 90 | 2.1 |
| 5 | 90 | 2.4 |
| 6 | 180 | 1.2 |
| 7 | 180 | 1.5 |
| 8 | 180 | 1.8 |
| 9 | 180 | 2.1 |
| 10 | 180 | 2.4 |
| 11 | 270 | 1.2 |
| 12 | 270 | 1.5 |
| 13 | 270 | 1.8 |
| 14 | 270 | 2.1 |
| 15 | 270 | 2.4 |

TABLE 2

Formulations of Enzyme Preparations.

| | Component | |
|---|---|---|
| Test Group | Transglutaminase (U) | Magnesium chloride (g) |
| 16 | 180 | 2.7 |
| 17 | 180 | 3.0 |
| 18 | 180 | 3.3 |
| 19 | 180 | 3.6 |
| 20 | 180 | 3.9 |
| 21 | 180 | 4.2 |

Each enzyme preparation so prepared was thoroughly mixed with small pieces of pork ham (about 2 cm cube, a total of 300 g), and the mixture was packed into a casing tube that had a folding width of 75 mm. The tube was left at 5° C. for 18 hours to allow the transglutaminase reaction to proceed. Thereafter, the tube was placed in a −40° C. freezer, and preserved therein for later evaluation. The frozen bound pork was then sliced into a thickness of 9 mm and a width of 25 mm.

Figure 2:
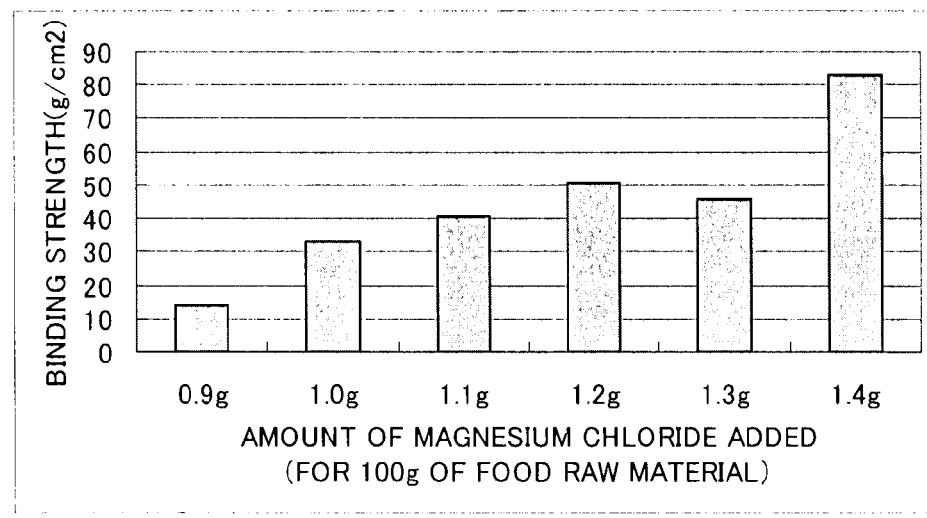
FIG. 2 is a diagram representing the relationship between the binding strength and the amounts of magnesium chloride and transglutaminase added (Example 1).

FIGS. 1 and 2 show the results of tensile strength measurements performed in the raw state with a rheometer (Fudo Kougyou) after thawing. In contrast to the tensile strength of 80 g/cm$^2$ as the conventional index of a practical binding strength measured in the same manner, the values of binding strength measured in this evaluation were above this reference value (80 g/cm$^2$) in the test groups that had the calcium chloride content of 2.1 g (0.7 g per 100 g of the food raw material) or more from among the test groups 1 to 5, and 6 to 10 in which the transglutaminase was added in 90 U and 180 U (30 U and 60 U per 100 g of the food raw material). The values of binding strength also exceeded the reference value in the test groups that had the calcium chloride content of 1.8 g (0.6 g per 100 g of the food raw material) or more from among the test groups 11 to 15 in which the transglutaminase was added in 270 U (90 U per 100 g of the food raw material). Further, the value of binding strength was above the reference value in the test group that had the magnesium chloride content of 4.2 g (1.4 g per 100 g of the food raw material) or more from among the test groups 16 to 21 in which magnesium chloride was added. As these results demonstrate, practical binding strength can be obtained by using calcium chloride, magnesium chloride, and transglutaminase in the appropriate ranges.

Comparative Example 1

Calcium oxide (calcined calcium), an inorganic salt of calcium as is calcium chloride, is known to bind food materials when added in appropriate amounts. Thus, it was investigated whether use of calcium oxide would provide the same effect obtained with the use of calcium chloride. Comparisons using various other salts were also made.

Each salt presented in Table 3 was dissolved in 12 ml of water with 180 units of transglutaminase, and, after the solution was thoroughly mixed with small pieces of pork ham (about 2 cm cube, a total of 300 g), the mixture was packed into a casing tube that had a folding width of 75 mm. The tube was left at 5° C. for 17 hours to allow the transglutaminase reaction to proceed. Thereafter, the tube was placed in a −40° C. freezer, and preserved therein for later evaluation. Thereafter, tensile strength was measured in the same manner as in Example 1, and comparison was made. The results are presented in Table 3.

As shown in Table 3, of all the groups in which 2.1 g of salt (0.7 g per 100 g of raw food) was added, binding was sufficient only in the calcium chloride-added group, and sufficient binding strength could not be obtained in groups that had other salts. The calcium oxide-added group had a binding strength close to a sufficient value; however, the meat turned white in color, and was not desirable in terms of appearance. The discoloration is considered to be due to the fact that calcium oxide is an alkali. The results therefore demonstrated that the binding technique using calcium oxide, being a calcium salt as well, was completely different from the binding technique using calcium chloride and transglutaminase, and that calcium oxide could not be used as a replacement of calcium chloride.

TABLE 3

| Salt | Amount added (for 300 g of meat) | Binding strength | Note |
| --- | --- | --- | --- |
| Calcium chloride | 2.1 g | 104.9 g/cm$^2$ | Good appearance |
| Calcium oxide | 2.1 g | 75.7 g/cm$^2$ | Turned white; undesirable |
| Calcium lactate | 2.1 g | — (Not bound) | — |
| Calcium gluconate | 2.1 g | — (Not bound) | — |
| Magnesium sulfate | 2.1 g | — (Not bound) | — |
| Potassium chloride | 2.1 g | — (Not bound) | — |
| Sodium chloride | 2.1 g | — (Not bound) | — |

INDUSTRIAL APPLICABILITY

With the enzyme preparation and the method for producing bound and formed food of the present invention, food raw materials such as meat pieces can be bound and formed sufficiently, without using casein, collagen, or other protein materials as auxiliary agents, and therefore it is highly useful in the field of food.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An enzyme preparation, comprising:
  (a) transglutaminase; and
  (b) calcium chloride or magnesium chloride,
  wherein:
    when present, said calcium chloride is present in an amount of 0.007 to 0.03 g per 1 U of the transglutaminase in said enzyme preparation,
    when present said magnesium chloride is present in an amount of 0.022 to 0.025 g per 1 U of the transglutaminase in said enzyme preparation.

2. An enzyme preparation according to claim 1, which comprises:
  (a) transglutaminase; and
  (b) calcium chloride,
  wherein said calcium chloride is present in an amount of 0.007 to 0.03 g per 1 U of the transglutaminase in said enzyme preparation.

3. A method for producing a bound and formed food, comprising treating one or more food raw materials with an enzyme preparation according to claim 2.

4. A bound and formed food, which is prepared by a method according to claim 3.

5. A method according to claim 3, wherein said one or more food raw materials is meat, and wherein said bound and formed food is bound and formed meat.

6. An enzyme preparation according to claim 1, which comprises:
  (a) transglutaminase; and
  (b) magnesium chloride,
  wherein said magnesium chloride is present in an amount of 0.022 to 0.025 g per 1 U of the transglutaminase in said enzyme preparation.

7. A method for producing a bound and formed food, comprising treating one or more food raw materials with an enzyme preparation according to claim 6.

8. A bound and formed food, which is prepared by a method according to claim 7.

9. A method according to claim 7, wherein said one or more food raw materials is meat, and wherein said bound and formed food is bound and formed meat.

10. A method for producing a bound and formed food, comprising treating one or more food raw materials with an enzyme preparation according to claim 1.

11. A method according to claim 10, wherein said one or more food raw materials is meat, and wherein said bound and formed food is bound and formed meat.

12. A bound and formed food, which is prepared by a method according to claim 10.

13. A method for producing a bound and formed food, comprising treating one or more food raw materials with about 0.6 g of calcium chloride and 75 to 100 units of trans-glutaminase per 100 g of said food raw material.

14. A method according to claim 13, wherein said one or more food raw materials is meat, and wherein said bound and formed food is bound and formed meat.

15. A bound and formed food, which is prepared by a method according to claim 13.

16. A method for producing a bound and formed food, comprising treating one or more food raw materials with 0.7 to 0.9 g of calcium chloride and 25 to 100 units of trans-glutaminase per 100 g of said food raw material.

17. A method according to claim 16, wherein said one or more food raw materials is meat, and wherein said bound and formed food is bound and formed meat.

18. A bound and formed food, which is prepared by a method according to claim 16.

19. A method for producing a bound and formed food, comprising treating one or more food raw materials with 1.4 to 1.6 g of magnesium chloride and 60 to 100 units of trans-glutaminase per 100 g of said food raw material.

20. A method according to claim 19, wherein said one or more food raw materials is meat, and wherein said bound and formed food is bound and formed meat.

21. A bound and formed food, which is prepared by a method according to claim 19.

* * * * *